United States Patent [19]

Berlant

[11] Patent Number: 5,070,862
[45] Date of Patent: Dec. 10, 1991

[54] GLOVE FOR ELECTRO-MASSAGE THERAPY

[76] Inventor: Stephen R. Berlant, 392 Marple Rd., Broomall, Pa. 19008

[21] Appl. No.: 209,432

[22] Filed: Jun. 21, 1988

[51] Int. Cl.[5] .............................................. A61H 1/00
[52] U.S. Cl. ................... 128/24.5; 128/420.5; 128/783; 128/798; 128/800
[58] Field of Search ..................... 128/24.5, 24.1, 784, 128/796, 798, 795, 783, 800, 788, 802, 420.5, 421

[56] References Cited

U.S. PATENT DOCUMENTS

| | | | |
|---|---|---|---|
| 206,474 | 7/1878 | Morel | 128/24.5 |
| 401,041 | 4/1889 | Lewin | 128/800 |
| 695,971 | 3/1902 | Turck | 128/24.5 |
| 1,536,273 | 5/1925 | Schnee | 128/62 R |
| 1,545,413 | 7/1925 | Elmvall | 128/24.5 |
| 1,915,721 | 6/1933 | Diaz | 128/24.5 |
| 3,055,372 | 9/1962 | Browner | 128/798 |
| 3,845,771 | 11/1974 | Vise | 128/800 X |
| 4,207,904 | 6/1980 | Greene | 128/798 |
| 4,367,755 | 1/1983 | Bailey | 128/798 |
| 4,458,696 | 6/1984 | Larimore | 128/798 |
| 4,510,939 | 4/1985 | Brenman | 128/800 |

FOREIGN PATENT DOCUMENTS 969374 12/1950 France .................. 128/800

*Primary Examiner*—Edgar S. Burr
*Assistant Examiner*—Moshe I. Cohen

[57] ABSTRACT

Apparatus for applying therapeutic electro-massage includes a flexible glove having a single electrode covering substantially the entire palmar surface of the glove. The electrode is formed of a non-metallic, electrically conductive, flexible material such as carbonized rubber. The electrode is connected to a source of pulsed electrical energy such as a TENS unit. The glove is used by a therapist to apply a combination of manual massage and electrical nerve stimulation to a patient.

3 Claims, 1 Drawing Sheet

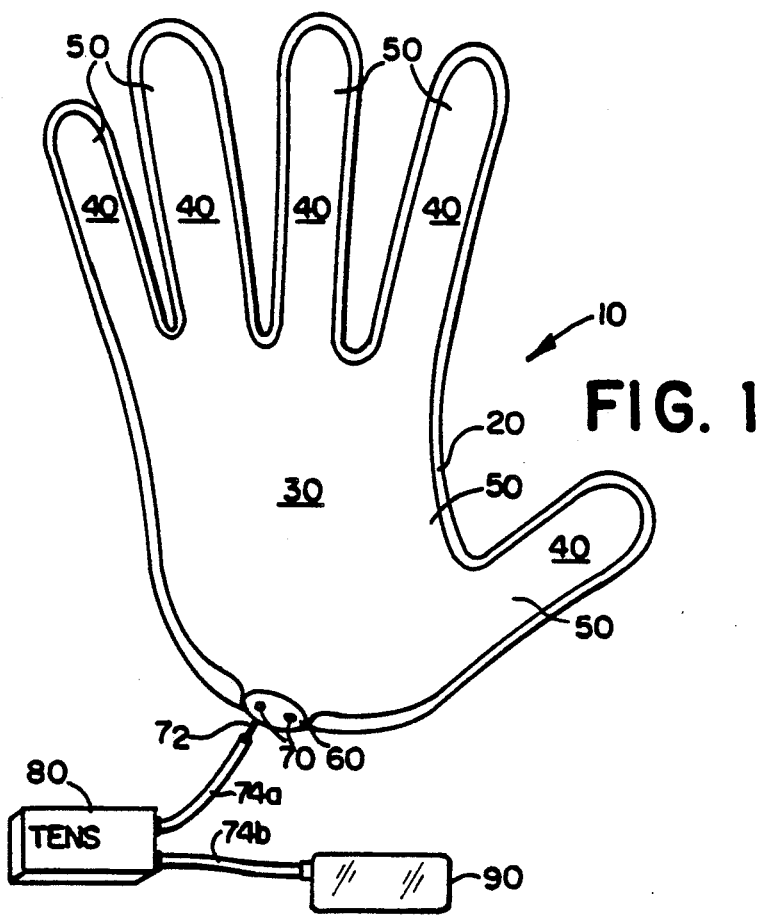
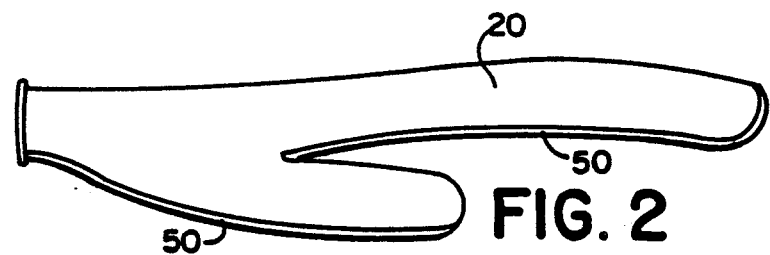
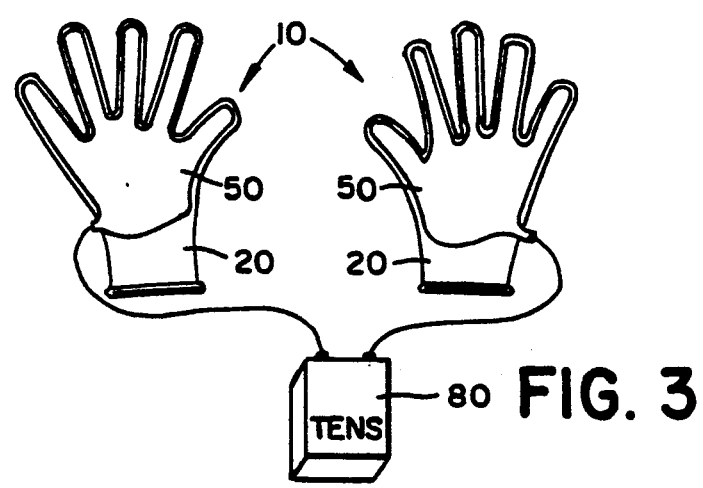

GLOVE FOR ELECTRO-MASSAGE THERAPY

BACKGROUND OF THE INVENTION

This invention relates generally to apparatus for application of therapeutic electro-massage and more particularly to an electrode glove for use by a therapist to effectively apply a combination of whole hand massage and electrical stimulation to a patient.

Transcutaneous electrical nerve stimulation (TENS) involves the delivery of electrical energy through human skin tissue to excite underlying nerves. It is known that the selective stimulation of the large, myelinated afferent nerve fibers in a painful area can reduce pain by altering the pattern of neural inputs to the spinal cord. It has also been suggested that TENS may provide pain relief by inducing the release of natural pain killers such as beta-endorphin. TENS is applied through electrodes which are affixed to the patient's skin. Although TENS has been used mainly to stimulate nerve fibers to relieve pain, it can also be use to elicit muscle contractions if sufficient energy is applied. Attempts have been made to combine the beneficial effects of transferring electrical energy to human tissue together with manual massage. However, known devices for such use leave much to be desired for performing electro-massage on the deep muscles of the neck, shoulders, or back.

When massaging the lower back, the therapist is required to apply pressure with the thenar and hypothenar eminence, commonly called the heel of the hand, together with the fleshy prominences covering the palmar surface of the metacarpal-phalangeal articulations, i.e. the palm-side of the knuckle joints. Accordingly, electrodes must be disposed on these surfaces to obtain effective electro-massage. Known devices for electro-massage such as those described in Brenman, U.S. Pat. No. 4,510,939; Shepard, U.S. Pat. No. 3,556,105; and Fournier, French Patent No. 967,374 have very small electrodes disposed on particular parts of the respective glove or mitten, such as the tips of specific fingers. The electrodes used for these devices are effectively point electrodes. Such small electrodes are undesirable for use with TENS because the high current densities resulting therefrom can cause burning of the skin tissue.

Furthermore, the above noted devices have the anode and cathode in close proximity. Such close proximity between the anode and cathode reduces the depth of current penetration in biological tissue. Additionally, there is a greater risk of shorting between the anode and cathode during hand movement.

Other gloves for electro-massage therapy have been devised with larger surface electrodes. However, all of these also have disadvantages. For example, an electrotherapeutic glove described in Elmvall, U.S. Pat. No. 1,545,413, has a plurality of small metallic electrodes wired together in a mesh which covers the palmar surface of the glove. The use of metallic electrodes directly on the skin, however, is undesirable because metallic ions may pass into the body with electric current. Also, the high resistance of the skin tends to convert electric energy into heat when bare metal makes contact with the skin, resulting in burning. Schnee U.S. Pat. No. 1,536,273, describes a mitten for therapeutic massage in which a conducting mesh is covered with a moisture absorbing fabric. Morell, U.S. Pat. No. 206,474, describes an electrode glove in which the metallic electrode is covered with sponge material. Such devices must be taken out of service to be washed after a single use. In the case of sponge material, the device cannot be easily cleaned at all and has a short life expectancy when repeatedly rubbed on the skin as is required in massage therapy.

Other types of electrode gloves such as described in Lewin, U.S. Pat. No. 401,041, and French Patent No. 446,865 have one or more wires disposed along the palmar surface of the glove which are covered with a moisture absorbing fabric such as cloth or leather. In addition to the problems of keeping such devices clean after use, the wire electrodes may break with repeated use and can pierce the fabric causing pain and possible injury to the patient.

All of the electrode gloves described above are difficult to fabricate because they include a combination of insulating materials, metallic conductors, and moisture absorbing fabrics. These varied materials are not easily assembled together and special manufacturing and assembling techniques are required.

SUMMARY OF THE INVENTION

It is a principal object of this invention to provide an electrode glove suitable for applying electro-massage with substantially the entire hand.

It is a further object of this invention to provide a glove for therapeutic electro-massage having an electrode which covers substantially the entire palmar surface of the therapist's hand.

Another object of this invention is to provide an electrode glove for electro-massage having a nonmetallic electrode.

A still further object of this invention is to provide an electrode glove which is easy to manufacture and can be reused frequently.

The above and other objects are realized in an electrode glove having a shell formed of an elastomeric, insulating material. The entire palmar surface of the glove is covered with a layer of nonmetallic, electrically conductive, flexible material and includes an integral connector for accepting one or more leads from a standard TENS unit. By applying electro-conductive gel to an area of a patient's body and connecting the glove to a TENS unit, a therapist can effectively apply a combination of manual massage and TENS to a patient.

DESCRIPTION OF THE DRAWINGS

FIG. 1 is a view of the palmar surface of an electrode glove according to the invention and apparatus for use therewith to apply electro-massage.

FIG. 2 is a side view of the electrode glove in FIG. 1 showing the electro-conductive layer.

FIG. 3 shows a two-glove embodiment of electro-massage apparatus according to the invention.

DETAILED DESCRIPTION OF THE APPARATUS

Referring now to the drawings, there is shown an electrode glove 10 according to the invention. The electrode glove 10 includes a shell 20 formed of a flexible elastomeric material such as latex rubber which is also electrically insulating. Substantially all of the palmar surface 30 of the glove including the surfaces 40 of the fingers and thumb are covered with a thin layer of an electrically conductive but nonmetallic, flexible material which constitutes an electrode 50. A connector 60 formed of the same material extends from one end of the electrode 50 preferably at the heel of the hand. The connector 60 is integral with the electrode 50 and includes one or more small holes 70 formed to accept the male connectors 72 on the lead wires 74a, 74b of a TENS unit 80.

The electrode 50 is fabricated from a thin layer of an elastomeric material such as carbonized rubber or carbonized silicone. An example of a suitable material is that manufactured and sold by Dow Corning under the name "Silastic". The electrode 50 is applied to the shell 20 with a proper adhesive or it may be deposited as a coating.

The TENS unit 80 is a small, portable, battery operated device which emits biphasic pulses having zero net direct current. The amplitudes of the pulses can be up to sixty milliamps with durations of up to 500 microseconds and pulse rates of up to 200 hertz. The current emitted by TENS units which are powered by higher voltages, for example 220 volt AC, can be much greater than those previously described. For example, one type of AC powered TENS unit known as a high voltage pulsed galvanic stimulator (HVPGS), is capable of emitting pulses of up to 500 volts. Another type of TENS unit known as the Russian Faradic Unit, can emit pulses at rates up to 2000 hertz. A special class of TENS unit known as a Functional Electrical Stimulation (FES) unit, is a battery operated unit which is specifically designed to elicit timed cyclical contractions to strengthen muscles or prevent atrophy from disuse.

The electrode glove according to the present invention provides a means for combining the therapeutic effects of TENS with the benefit of manual massage when the glove is connected to a TENS, FES, or HVPGS unit. In operation, and as shown in FIG. 1, one lead wire 74a from a TENS unit output channel is connected to energize the glove electrode 50, while the other lead wire 74b is connected to energize a large indifferent electrode 90 attached to the patient. In another operative mode as shown in FIG. 3, an electrode glove 10 according to the invention may be worn on each hand with one glove connected to the anode of a TENS unit output channel and the other glove connected to the cathode of the channel.

If more power than is normally available from a single channel of a TENS unit is needed, the lead wires of similar polarity from each channel of a dual channel unit which has output channels that fire synchronously may be connected to one glove electrode and the remaining lead wires of similar polarity may be connected to the other glove electrode or an indifferent electrode.

Some of the many novel features and advantages of the present invention are now apparent in view of the foregoing discussion. For example, an electrode glove having a single electrode covering substantially the entire palmar surface and fingers of the glove shell has been described which permits a therapist to apply deep electro-massage with substantially the entire hand. The electrode is formed of a thin layer of conductive, non-metallic, flexible material which is bonded to or deposited on the palmar surface of the glove. The glove electrode is connected to one lead of a TENS output channel, the other lead being connected to another such electrode glove or an indifferent electrode. Thus, the stimulating electrodes can be significantly separated from each other to permit maximum current penetration and prevent shorting between the electrodes. The substantial electrode surface provided by this invention minimizes increases in current density which can result from small point type electrodes used in known devices. The invention is simpler to fabricate because its entire palmar surface is covered with a single homogeneous conductive material designed to contact biological tissue. This material is easily cleaned with soap and water after use. It is easily bondable to the elastomeric material of the glove shell and thus no metallic electrodes need be used.

It will be recognized by those skilled in the art that changes or modifications may be made to the above described embodiment without departing from the broad inventive concepts of the invention. It is understood therefore that the invention is not limited to the particular embodiment which is described, but is intended to cover all modifications and changes within the scope and spirit of the invention as defined in the appended claims.

What is claimed is:

1. Apparatus for applying deep electro-massage for use with a transcutaneous electrical nerve stimulation (TENS) unit comprising: a glove covering substantially all of the palm, fingers and thumb of a hand, said glove being formed of a flexible, electrically insulating layer of material capable of insulating the hand against pulsed, direct currents at a voltage of up to 500 volts;
   an electrode affixed to and covering substantially all of the palm and the palmar surface of the fingers and thumb of said glove, said electrode being formed of a non-metallic, electrically conductive, flexible layer deposited as a coating; and
   a connector means disposed on said electrode for connecting said electrode to a TENS unit.

2. Apparatus as recited in claim 1 wherein said electrode is formed of an elastic material.

3. Apparatus for applying deep electro-massage for use with a transcutaneous electrical nerve stimulation (TENS) unit comprising: a hand-covering for covering substantially all of the palm, fingers and thumb of a hand, said hand-covering being formed of an electrically insulating layer of material capable of insulating the hand against pulsed, direct currents at a voltage of up to 500 volts;
   an electrode covering substantially all of the palm and the palmar surface of the fingers and thumb of said glove, said electrode being formed of a non-metallic, flexible, electrically conductive layer deposited as a coating so as to be integrally formed with said hand-covering; and
   a connector means affixed on said electrode for connecting said electrode to a TENS unit.

* * * * *